United States Patent
Starta et al.

(10) Patent No.: US 7,367,831 B2
(45) Date of Patent: May 6, 2008

(54) CONNECTORS, INSTRUMENT ASSEMBLIES AND METHODS OF CONNECTING OR DISCONNECTING ELECTRICAL CONNECTIONS UNDER POWER

(75) Inventors: Christopher D. Starta, Pittsburgh, PA (US); Bruce P. Apel, Pittsburgh, PA (US); Leonard J. Blatnica, New Kensington, PA (US); Scott A. Turner, Pittsburgh, PA (US); Dennis D. Mast, Zelienople, PA (US); Jeffrey L. Weber, Butler, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 0 days.

(21) Appl. No.: 10/841,852

(22) Filed: May 7, 2004

(65) Prior Publication Data
US 2004/0209507 A1    Oct. 21, 2004

Related U.S. Application Data

(63) Continuation of application No. 10/161,488, filed on May 31, 2002, now Pat. No. 6,799,984.

(51) Int. Cl.
*H01R 13/69* (2006.01)
(52) U.S. Cl. .................................... 439/246
(58) Field of Classification Search ........ 439/246–248, 439/139, 126, 312
See application file for complete search history.

(56) References Cited

U.S. PATENT DOCUMENTS 3,475,570 A    10/1969  Appleton
3,789,346 A  *  1/1974  De Brick ................. 439/283
4,162,816 A  *  7/1979  Malsot .................... 439/246
4,198,110 A  *  4/1980  Wetmore et al. ......... 439/321
4,525,610 A     6/1985  Le Magourou
5,284,566 A  *  2/1994  Cuomo et al. ........... 204/412

FOREIGN PATENT DOCUMENTS

GB    980811    1/1965
GB    2327125   1/1999
GB    2344467   6/2000

* cited by examiner

*Primary Examiner*—Alexander Gilman
(74) *Attorney, Agent, or Firm*—James G. Uber, Esq.; Henry E. Bartony, Jr., Esq.

(57) ABSTRACT

A connector includes a first housing section having a plurality of electrically conductive contacts therein. The connector also includes a second housing section including a plurality of electrically conductive contacts that can form an electrical connection with the contacts of the first housing section. The first housing section and the second housing section are removably connectable and are capable of forming an explosion proof or flame proof housing when connected. The contacts of at least one of the second housing section and the first housing section are movable relative to their respective housing section to align the contacts of the second housing and the contacts of the first housing section during connection of the second housing section to the first housing section. Electrically conductive connection between the contacts of the first housing section and the contacts of the second housing section occurs during connection such that when connection between the contacts of the first housing section and the contacts of the second housing section occurs, the first housing section and the second housing section are in sufficient connection to form an explosion proof housing.

19 Claims, 7 Drawing Sheets

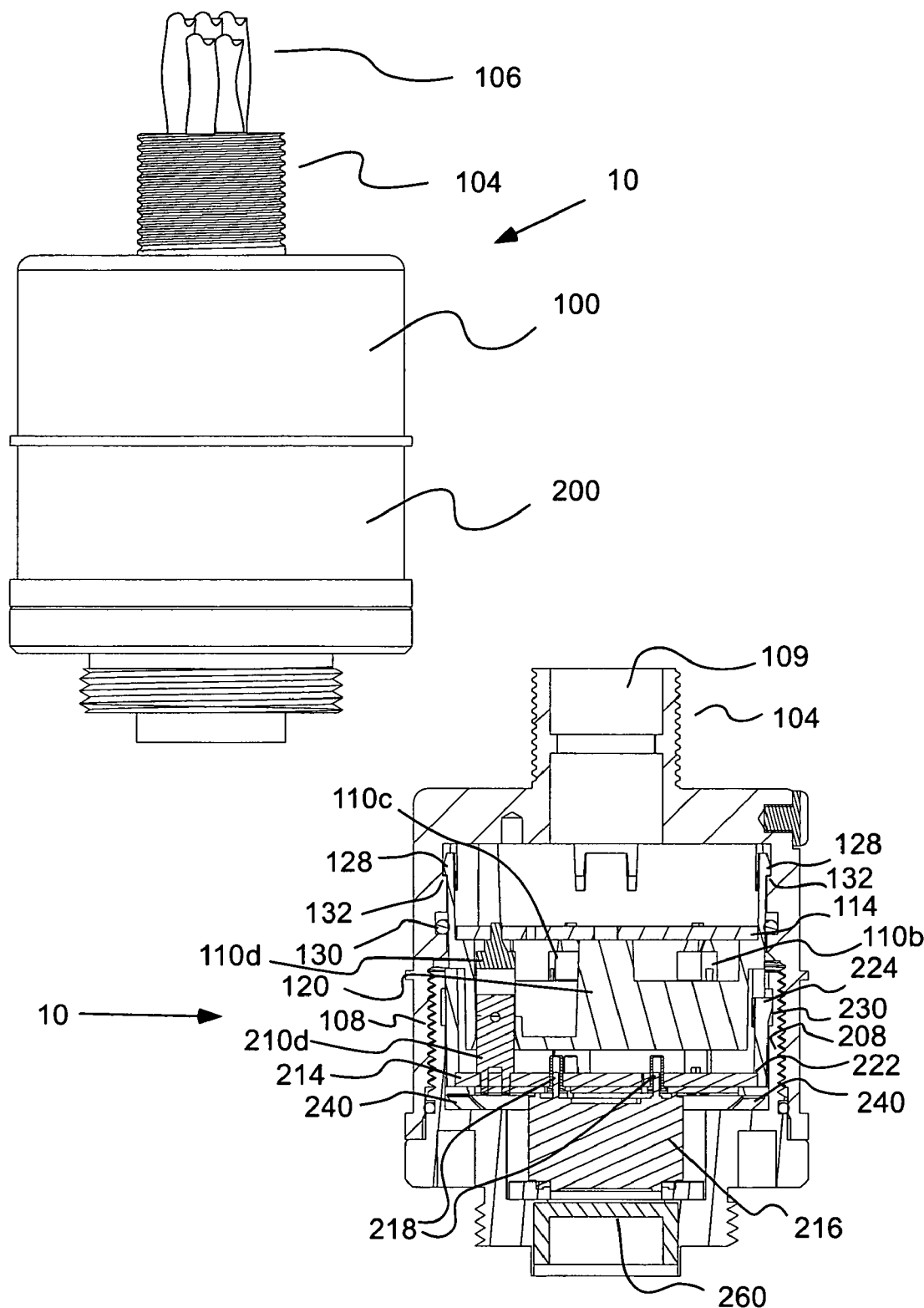

Fig. 6A
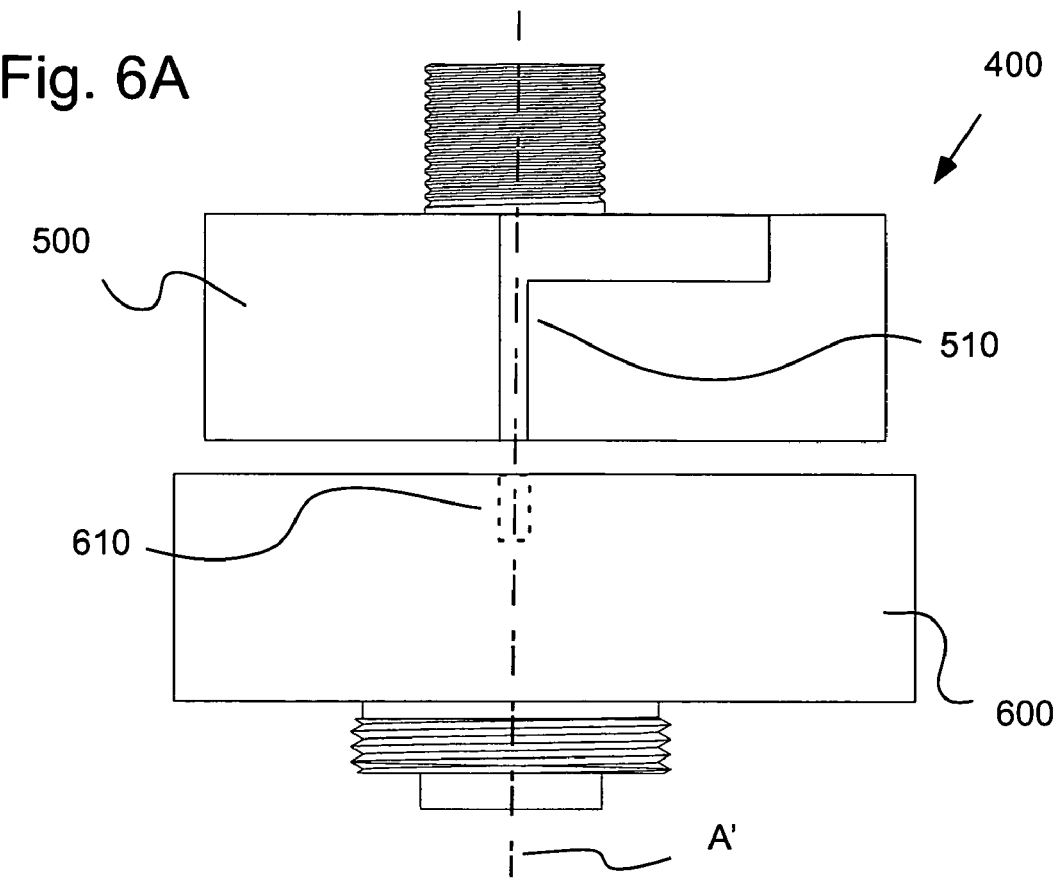
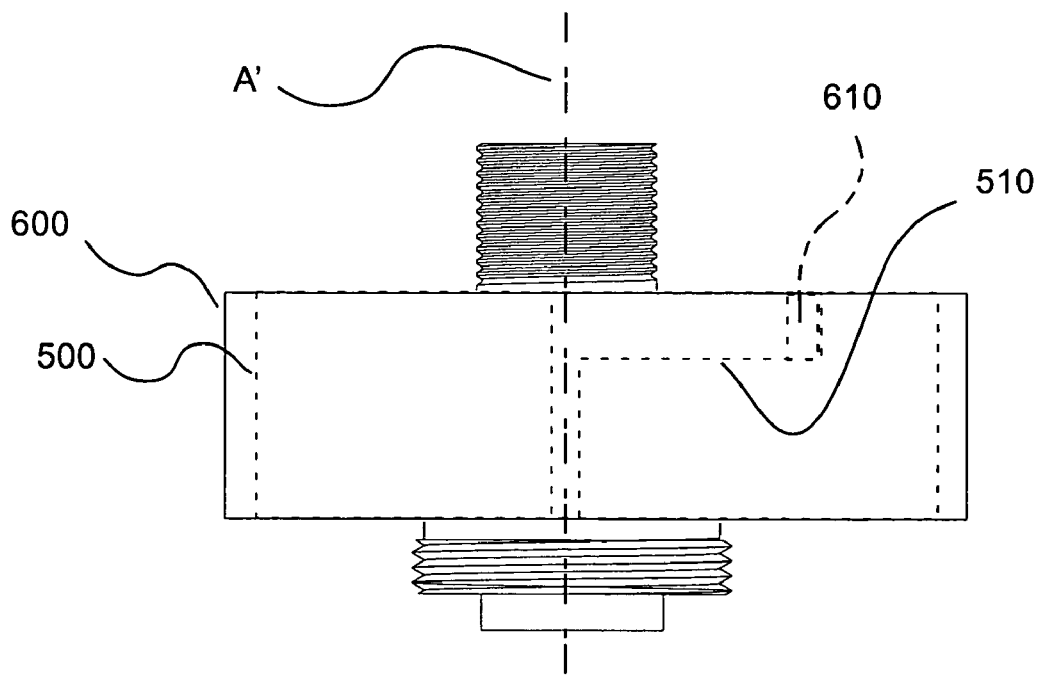
Fig. 6B

CONNECTORS, INSTRUMENT ASSEMBLIES AND METHODS OF CONNECTING OR DISCONNECTING ELECTRICAL CONNECTIONS UNDER POWER

CROSS-REFERENCE TO RELATED APPLICATIONS

This application is a continuation of U.S. patent application Ser. No. 10/161,488 filed on May 31, 2002 now U.S. Pat. No. 6,799,984.

BACKGROUND OF THE INVENTION

The present invention related to connectors, instrument assemblies and methods for connecting and/or disconnecting electrical connections under power. For example, the present invention relates particularly to sensor assemblies which can be connected and/or disconnected under power and to methods of connecting and/or disconnecting sensor assemblies under power. The connectors, instrument assemblies and methods of the present invention permit connection and/or disconnection under power such that the risk of igniting combustible or explosive gases in the surrounding environment is reduced and preferably eliminated.

In a hazardous environment, instruments are designed and installed in such a way that any source of ignition the instruments might produce is prevented from igniting combustible gases and/or other combustible materials in the surrounding atmosphere. For example, the device can be placed inside an explosion proof/flame proof enclosure, or the device circuitry can be made intrinsically safe. Intrinsically safe circuits are generally designed to have limited energy and are unlikely to produce an ignition source. Explosion proof/flame proof enclosures are generally designed with enough strength to withstand an internal explosion while guarding the external atmosphere from the ignition source.

When performing maintenance on an instrument installed in a hazardous environment, a user may desire to disconnect one or more assemblies or components such as a gas sensor. To perform such maintenance under current practice, the user can either declassify the area by removing all combustible or explosive gases therefrom or by removing power from the instrument to prevent the possibility of spark ignition creating an explosion or fire. Either of those choices costs the user significant time and money. Declassification or power interruption, however, may not be necessary if the instrument includes intrinsically safe circuitry which limits potential ignition energy. Although use of intrinsically safe circuitry is convenient for the user, the circuitry is more complex, costs more, and may have a power limit that does not satisfy all desired applications.

In the mining industry, the Gedcon Model 2400 Permissible Explosion-proof Connector manufactured by General Energy Development Corp. of Needham, Mass. purports to provide an explosion-proof connector for coupling two sections of multiple wire cable in which disconnection of the electrical contacts can be made with the explosion proof nature of the connector intact. That connector is also the subject of U.S. Pat. No. 4,198,110. That connector includes a receptacle housing having an insulative receptacle locked in position therein. A cooperating plug is likewise locked in position in a plug housing. An elongated dagger pin 36 in the plug housing cooperates with a receptacle in the receptacle housing to align male contact pins of the plug with the female contact sockets of the receptacle. A sleeve extends at least partially over both housings and threadingly engages with one of the housings to maintain engagement between the plug and receptacle when the sleeve is tightened. Requiring alignment of the elongated dagger pin with the cooperating receptacle to mate the contacts within the two housings of the connector during connection can be very difficult and substantially reduces the utility of that connector in an instrument assembly and elsewhere. Thus, the connector of U.S. Pat. No. 4,198,110 is generally difficult and complicated to connect properly, particularly under conditions typical of instrument assemblies installed in hazardous environment. Such instrument assemblies are often mounted on surfaces in locations which are not easily accessible.

It is desirable, therefore, to develop explosion proof connectors (for use, for example, in instrument assemblies installed in hazardous environments) and methods of connection and/or disconnection that reduce or eliminate the above-described and other problems with current connectors.

SUMMARY OF THE INVENTION

In one aspect, the present invention provides a connector or a housing for use in an environment in which a combustible material (for example, a combustible gas, a combustible dust or a combustible fiber) may be present. The connector includes a first housing section having a plurality of electrically conductive contacts therein. The connector also includes a second housing section including a plurality of electrically conductive contacts that can form an electrical connection with the contacts of the first housing section. The first housing section and the second housing section are removably connectable. The first housing section and the second housing section are capable of forming an explosion proof or flame proof (referred to collectively herein as explosion proof) housing when connected. The contacts of at least one of the second housing section and the first housing section are movable relative to their respective housing section to align the contacts of the second housing and the contacts of the first housing section during connection of the second housing section to the first housing section. Electrically conductive connection between the contacts of the first housing section and the contacts of the second housing section occurs during connection of the second housing section to the first housing section in a manner such that when connection between the contacts of the first housing section and the contacts of the second housing section occurs, the first housing section and the second housing section are in sufficient connection to form an explosion proof housing.

The contacts of the first housing section can, for example, be in electrical connection with a first cable (for example, a multiple-wire connector) and the contacts of the second housing section can, for example, be in electrical connection with a second cable.

Moreover, the connector of the present invention can also form an instrument housing wherein one of the first housing section and the second housing section includes at least one instrument component in electrical connection with the contacts of that housing. At least one of the contacts of the other of the first housing section and the second housing section is adapted to transmit electrical power to the instrument component when the first housing section and the second housing section are connected.

In another aspect, the present invention provides a method of forming a connection between electrically conductive contacts in an environment in which a combustible material may be present, including the steps of:

(a) connecting a second housing section, including a plurality of electrically conductive contacts that can form an electrical connection with a plurality of electrically conductive contacts of a first housing section, to the first housing section;

(b) permitting at least one of the plurality of contacts of the second housing section and the plurality of contacts of the first housing section to move relative to their respective housing section to align the contacts of the second housing and the contacts of the first housing section during connection of the second housing section to the first housing section, and (c) making electrically conductive connection between the contacts of the second housing section and the contacts of the first housing section during connection of the second housing section to the first housing section in a manner such that when connection between the contacts of the first housing section and the contacts of second housing section occurs, the first housing section and the second housing section are in sufficient connection to form an explosion proof housing.

In still a further aspect, the present invention provides a gas sensor assembly for use in an environment in which a combustible material may be present including a first housing section having a plurality of electrically conductive contacts therein. At least one of the contacts of the first housing section is electrically connectible to a power source. The contacts of the first housing section can, for example, be seated in a slotted, protective cover to prevent inadvertent contact with other conductive devices when the first housing section and a second housing section are disconnected.

The gas sensor assembly also includes a second housing section preferably having a plurality of electrically conductive contacts that can form an electrical connection with the contacts of the first housing section. At least one of the contacts of the second housing section is in electrical contact with a gas sensor. The first housing section and the second housing section are removably connectable and are capable of forming an explosion proof housing when connected. The contacts of at least one of the second housing section and the first housing section are movable relative to their respective housing section to align the contacts of the second housing and the contacts of the first housing section during connection of the second housing section to the first housing section. As described above, electrically conductive connection between the contacts of the first housing section and the contacts of the second housing section occurs during connection of the second housing section to the first housing section in a manner such that when connection between the contacts of the first housing section and the contacts of second housing section occurs, the first housing section and the second housing section are in sufficient connection to form an explosion proof housing.

Preferably, electrical connection between the contacts of the first housing section and the contacts of the second housing section is broken during disconnection of the second housing section from the first housing section in a manner such that when disconnection between the contacts of the first housing section and the contacts of second housing section occurs, the first housing section and the second housing section remain in sufficient connection to form an explosion proof housing.

In one embodiment, the second housing section is moved axially away from the first housing section during disconnection and the second housing section is moved axially toward the first housing section during connection. The second housing section can, for example, include threading that cooperates with threading on the first housing section so that rotating the second housing section relative to the first housing section causes relative axial movement between the second housing section and the first housing section. In one embodiment, the second housing section includes a seating member to which the contacts of the second housing are attached. The seating member is rotatably attached to the second housing member. The seating member includes an abutment member that abuts an abutment member of the first housing section to prevent rotation of the seating member of the first housing section relative to the second housing section when the contacts of the second housing section are in a predetermined alignment with the contacts of the first housing section during connection of the second housing section to the first housing section.

The instrument assemblies and methods of the present invention eliminate the need to declassify an area or the need to interrupt or disconnect power to an instrument during connection and/or disconnection of certain housing sections and associated internal electrical contacts thereof by extending the use of an explosion proof enclosure. Because electrical contact of one or more components within the instrument are connected and/or disconnected while the integrity of the explosion proof enclosure remains intact, any spark thereby created cannot ignite any combustible gases in the external atmosphere. For example, a sensor or other component can be removed for replacement or repair without risk of ignition. Once the housing sections of the instrument are disconnected and the sensor or other internal components are removed, the electrical contact(s) that remain under power are preferably protected from damage or short circuit by a protective, insulating or nonconductive cover, or by being recessed. Replacement of a sensor or other instrument assembly and reconnection of the housing sections of the instrument are accomplished in a similar manner.

Preferably, as the sensor or other internal component is replaced and the housing sections of the instrument are reconnected, contacts associated with the housing sections are automatically aligned regardless, for example, of the relative rotational alignment of the housing sections at the beginning of connection, to prevent improper mating or connections. Polarization or unique alignment of one or more of the contacts can be used for additional assurance that proper alignment is achieved. The self-alignment of the contacts of the housing sections during connection thereof facilitates assembly of the connectors of the present invention. Indeed, such connectors are well suited for use in hazardous environments by industrial workers who may be wearing personal protective equipment.

In general, as a sensor or other instrument assembly of an instrument of the present invention is installed, the explosion proof properties of the enclosure are achieved first, then connection between the electrical contacts is made so that any potential ignition sources are contained within the explosion proof enclosure. As a result, intrinsically safe circuitry and any associated power limitations are not necessary. Moreover, power interruption to the instrument is not required, thereby saving the end user time and money while providing more options than currently are available.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 5A illustrates a side view of the sensor housing assembly of FIG. 1.

FIG. 5B illustrates a side, cross-sectional and partially cutaway view of the sensor housing assembly of FIG. 1.

FIG. 6A illustrates a side view of another embodiment of a sensor housing assembly of the present invention including a labyrinth connection in which the first housing section and the second housing section are in a disconnected state.

FIG. 6B illustrates a side view of the sensor housing assembly of FIG. 6A in which the first housing section and the second housing section are in a connected state.

DETAILED DESCRIPTION OF THE INVENTION

The present invention is described, for example, in connection with FIGS. 1 through 7B in which gas sensor assemblies are used as representative examples of instrument assemblies of the present invention which can be connected and/or disconnected while under power in an environment in which a combustible material (for example, a combustible gas, dust or fiber) is present without posing an ignition risk. One skilled in the art will recognize that instrument assemblies other than gas sensor assemblies can be made connectible and/or disconnectible under power in the manner described for the gas sensor assemblies of FIGS. 1 through 7B. Similarly, the present invention has applicability to the connection and/or disconnection of wires or cables under power. As is clear to one skilled in the art, the housings shown in FIGS. 1-3 could just as easily be the mating ends of two wires or cables.

Figure 1:
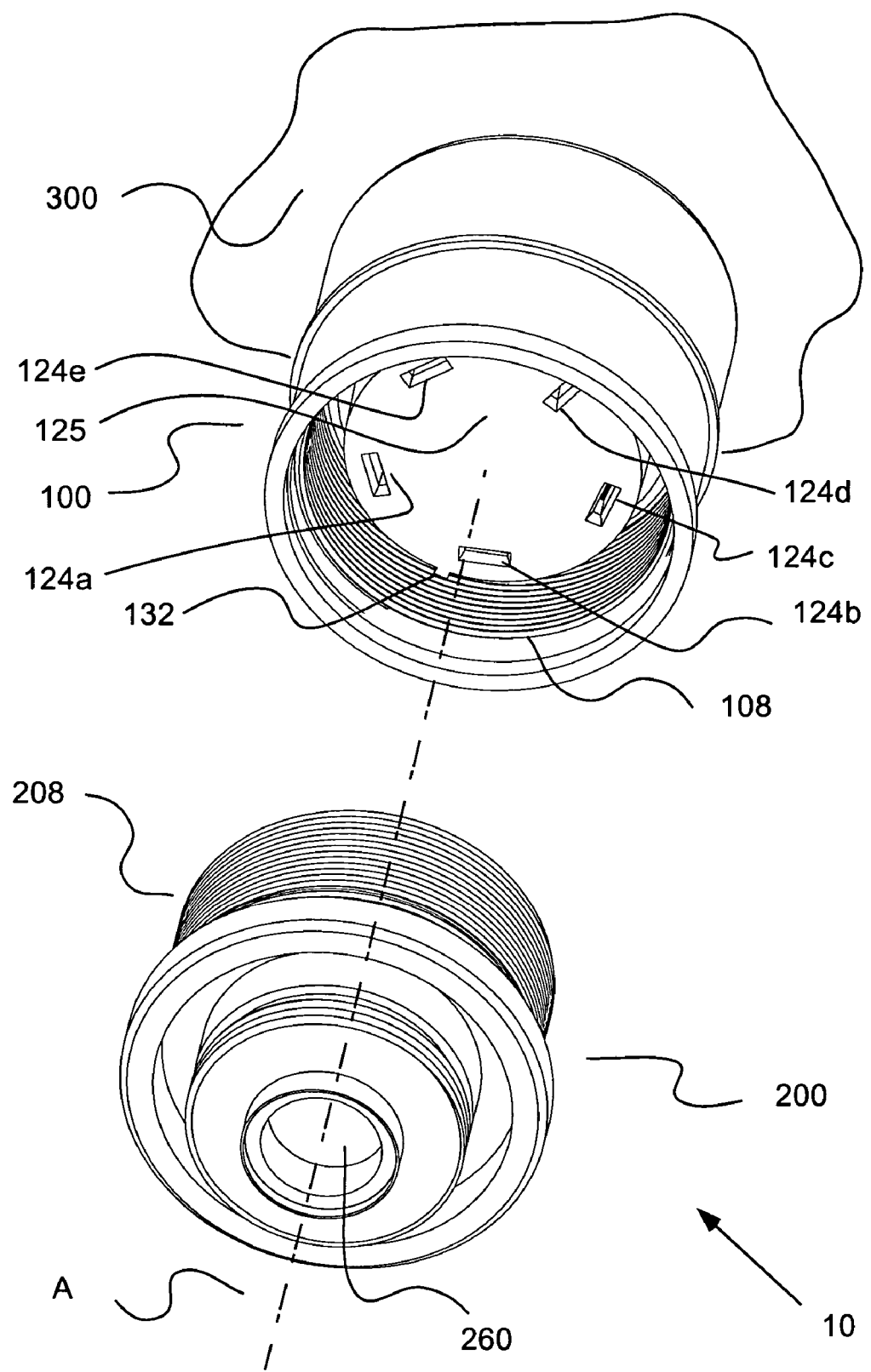
FIG. 1 illustrates a front perspective view of one embodiment of a sensor housing assembly of the present invention in which the first and second housing sections are in a disconnected state.
Figure 2:
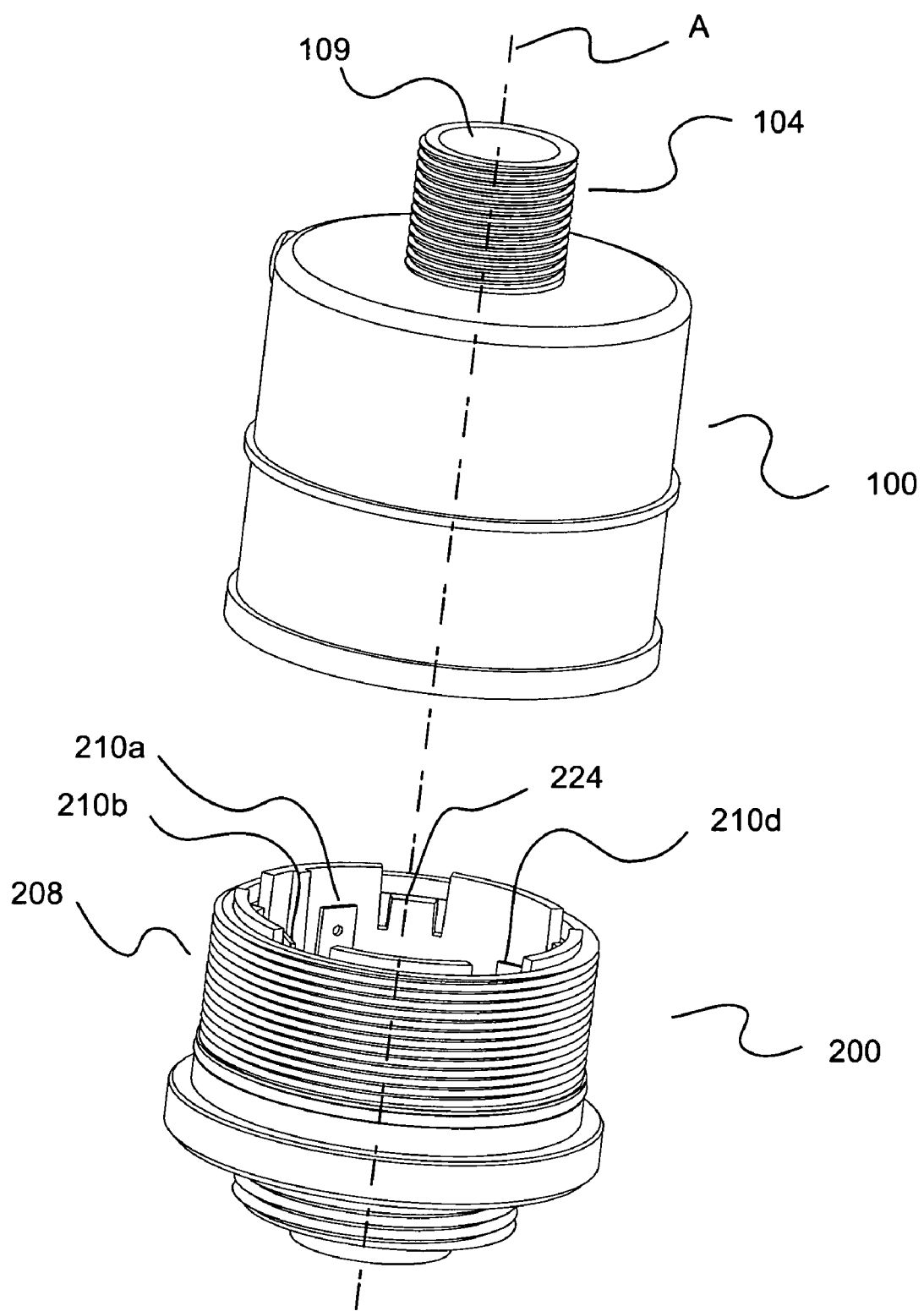
FIG. 2 illustrates another perspective view of the sensor housing assembly of FIG. 1 in which the first and second housing sections are in a disconnected state.
Figure 3:
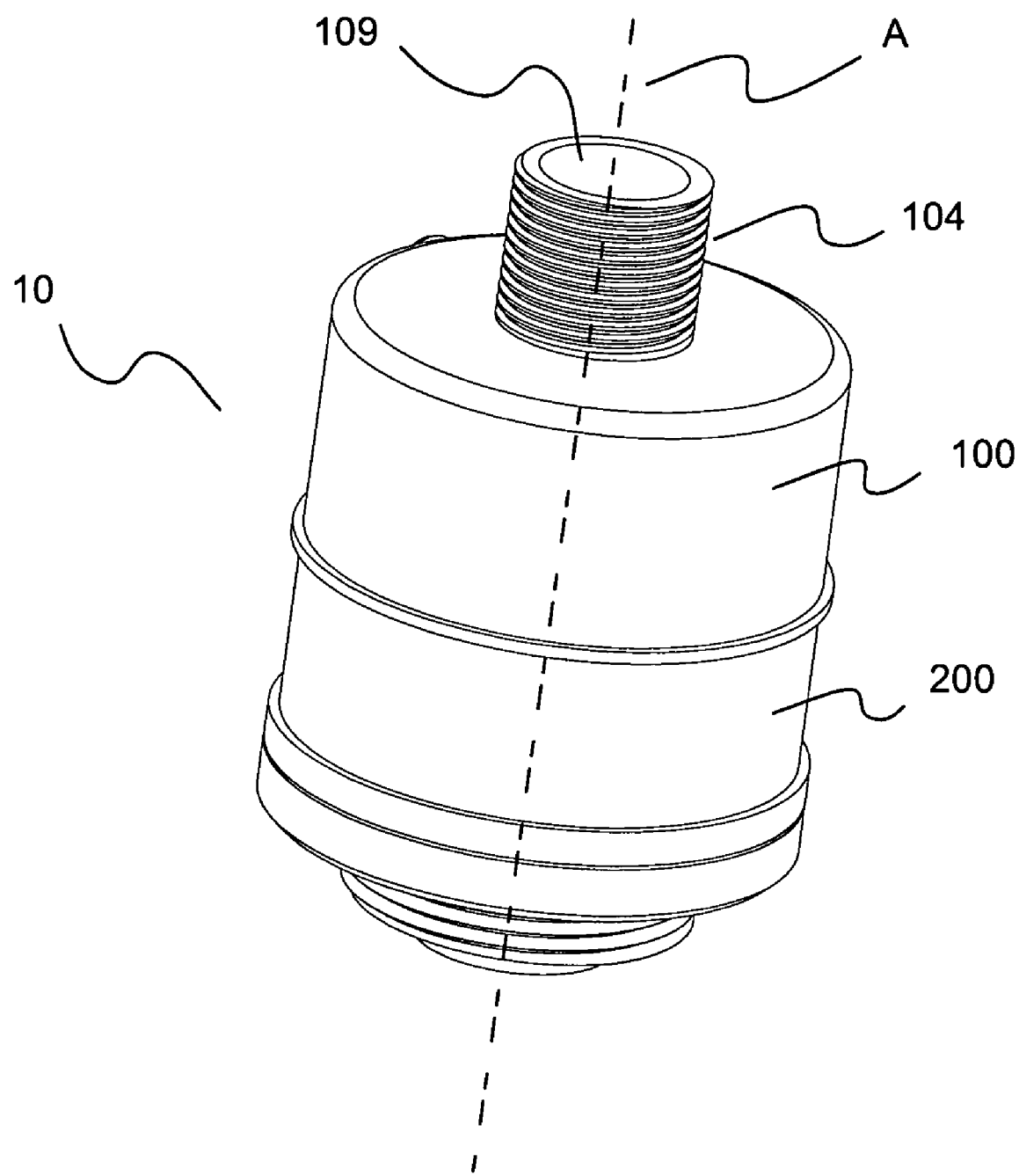
FIG. 3 illustrates a perspective view of the sensor housing assembly of FIG. 1 in which the first and second housing sections are in a connected state.
Figure 4:
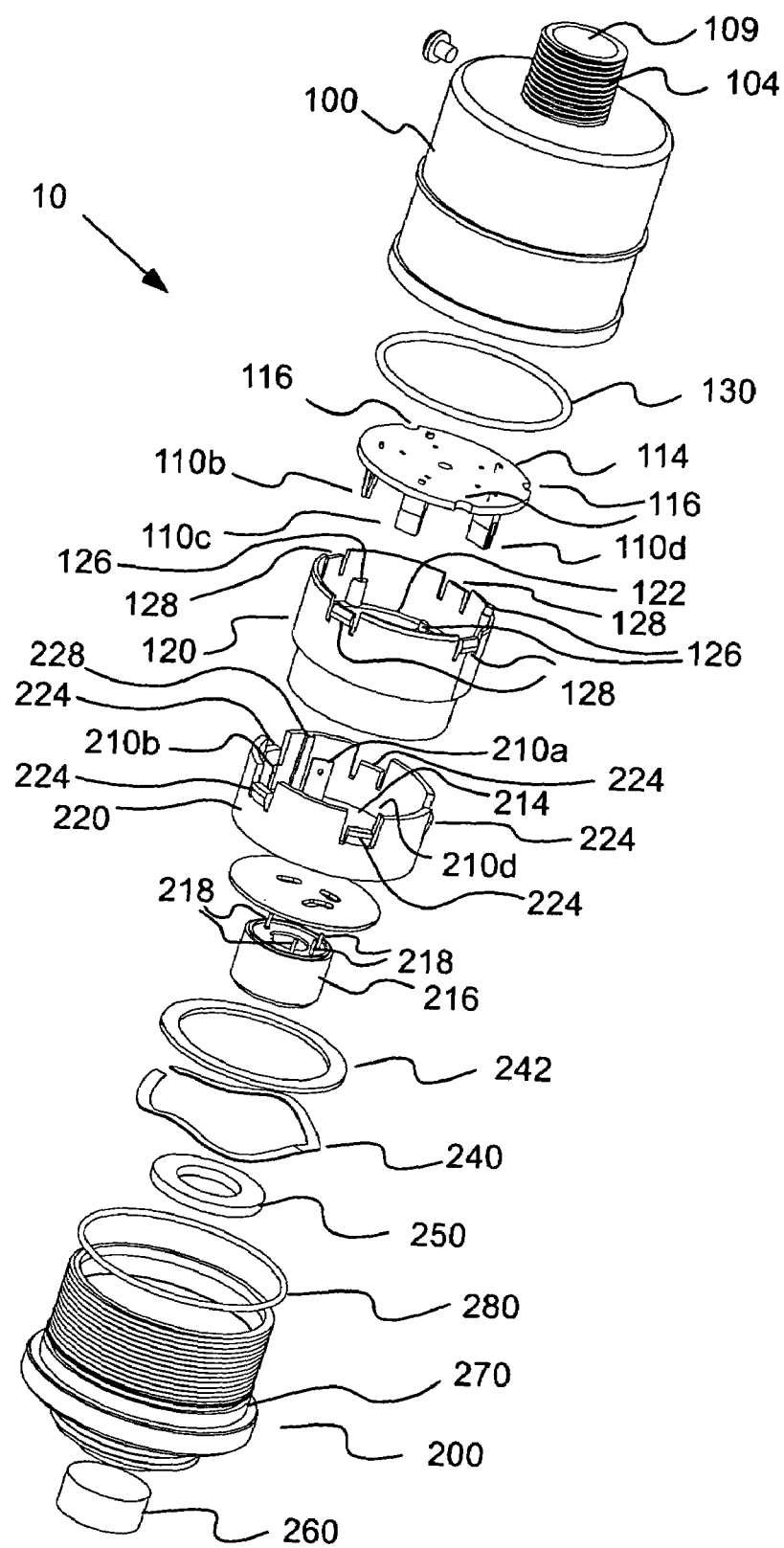
FIG. 4 illustrates a perspective view of the sensor housing assembly of FIG. 1 in a disassembled or exploded state.
Figure 7A:
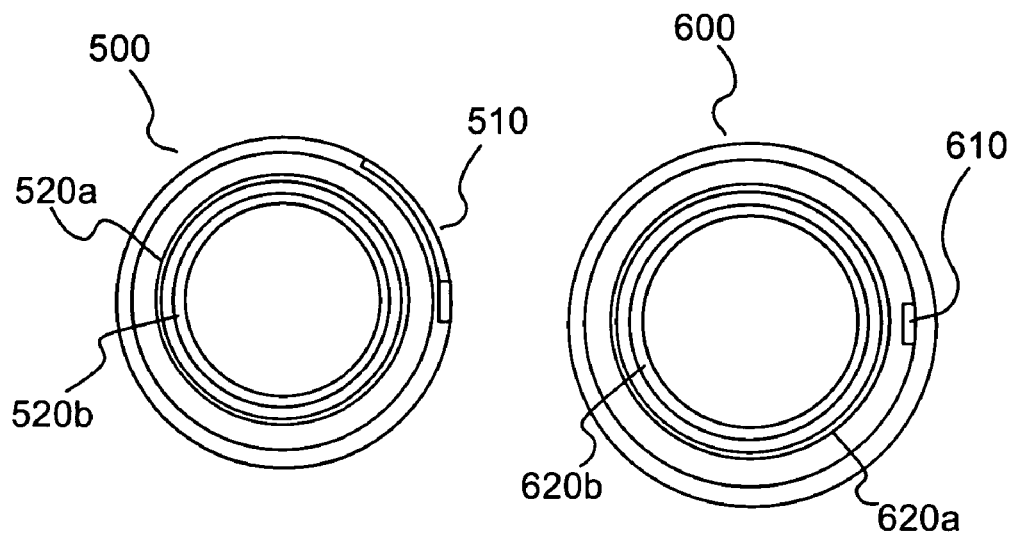
FIG. 7A illustrates a front view of the first housing section of the sensor housing assembly of FIG. 6A and a rear view of the second housing section of the sensor assembly of FIG. 6A.
Figure 7B:
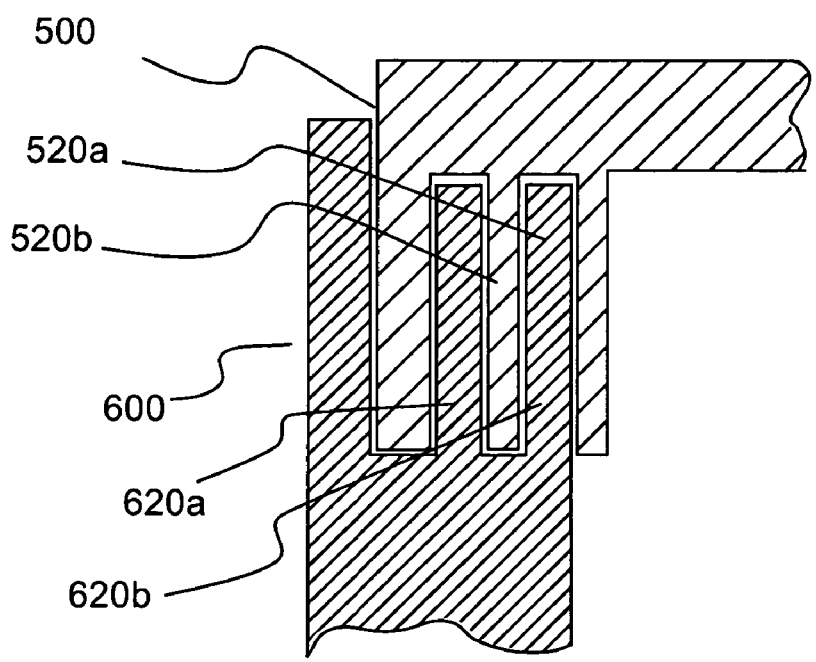
FIG. 7B illustrates a side, cross-sectional view of a portion of the first and second housing sections of the sensor housing assembly of FIG. 6A in a connected state.

FIGS. 1 through 5B illustrate one embodiment of a gas sensor assembly 10 of the present invention including a generally cylindrical first housing member or section 100 and a generally cylindrical second housing member or section 200. First housing section 100 and second housing section 200 can, for example, be fabricated from stainless steel. First housing section 100 can, for example, be fixed to a wall section 300 as illustrated in FIG. 1 via a connector such a threaded section 104 (see, for example, FIG. 2). Wires 106 (see FIG. 5A) can pass through a passage 109 in connector 104 to connect sensor assembly 10 to a variety of electrical devices such as, for example, a power source, measurement circuitry, a display or a communication system. A sealant is preferably contained in passage 109 and around wires 106 to assist in forming an explosion proof and flame proof housing within sensor assembly 10.

First housing section 100 and second housing section 200 are connectible via a threaded section 108 formed around the interior wall of housing section 100 and threaded section 208 formed around the exterior wall of housing section 200. The position of the threading can be reversed—that is, threading can alternatively be formed on the exterior of housing section 100 and the interior of housing section 200. In that regard, housing sections 100 and 200 are generally aligned to be coaxial and then brought together to make contact between threaded section 108 and threaded section 208. Housing section 200 can then be rotated in a clockwise direction relative to housing section 100 to draw housing sections 100 and 200 together in an axial direction. Of course, the direction of threading can also be reversed.

As used herein as a convention in, for example, connection with the discussion of FIGS. 1 through 5B, the terms "axial" or "axially" refer generally to, for example, an axis A or a similar axis (see, for example, FIGS. 1 through 3) around which sensor assembly 10 is formed (although not necessarily symmetrically therearound) and to directions collinear with or parallel to such an axis. The terms "rear" or "rearward" refer generally to an axial or a longitudinal direction toward threaded connector 104 of sensor assembly 10. The terms "front" or "forward" refers generally to an axial or a longitudinal direction away from connector 104 and toward metal frit 260 of housing section 200. The terms "radial" or "radially" refer to a direction normal to axis A.

Sensor assembly 10 and other instruments assemblies of the present invention further include at least one set of cooperating or mating electrical contacts (that is, at least one contact on each of, for example, housing sections 100 and 200 that cooperate or mate to form an electrical connection therebetween when housing sections 100 and 200 are connected. In general, sensor assemblies such as sensor assembly 10 include a plurality of contacts or contact members. Typically, at least three sets of contact members (that is, three contact members on each housing section) are preferably present in a sensor assembly to provide for a power connection, a ground connection and a data connection.

For example, sensor assembly 10 preferably includes contacts 110a-e (five in the representative embodiment of FIGS. 1 through 5B) attached to a circuit board 114 of sensor assembly 10. Two of contacts 110a-e are power contacts which may be of a different voltage: one contact is a ground contact; one contact is a data transmission contact; and one contact is a data reception contact.

Circuit board 114 and contacts 110a-e preferably are in electrical communication with a variety of electrical components such as, for example, a power source, measurement circuitry, a display (not shown), via wires 106 as described above. Circuit board 114 and contacts 110a-e are preferably seated in a seating or protective member 120 (formed, for example, from an insulating polymeric material) wherein a forward surface of circuit board 114 abuts a ledge 122 formed around the interior of seating member 120. Seating member 120 preferably includes a plurality of slots 124a-e in a forward surface 125 thereof that align with contacts 110a-e when circuit board 114 is seated within seating member 120. Seating member 120 can, for example, include guides 126 that cooperate with notches 116 formed in circuit board 114 to properly align circuit board 114 within seating member 120 so that slots 124a-e are generally aligned with contacts 110a-e. Seating member 120 preferably includes one or more connectors such as flexing tabs 128 that form a secure connection with housing section 100. Tabs 128, for example, form a snap fit with a groove or flange 132 (see FIG. 5B) formed around the interior wall of housing section 100.

A potting material (not shown) such as a dielectric polyurethane resin can be used to, for example, decrease void volume as well as to insulate, protect (for example, providing chemical resistance) and secure circuit board 114 within seating member 120. The potting material can, for example, be poured into housing section 100 via passage 109 after seating member 120 is secured to housing section 100. A seal can be formed between seating member 120 and housing section 100 via, for example, an O-ring 130 to prevent the potting resin from passing around seating member 120. Once, for example, the polyurethane resin is poured into the rear of seating member 120, it can be hardened by drying under heat.

Housing section 200 includes contacts or contact members 210a-d that are attached to a rear side of printed circuit board 214. In the embodiment of FIGS. 1 through 5B, each of contacts 110a-e is a female electrical contact including two closely adjacent, axially forward projecting metal members, and each of contacts 210a-210d is a male electrical contact including a single axially rearward projecting metal member that slides between the two metal members of one of corresponding contacts 110a-110d when electrical connection is made therebetween. Of course, the male and female nature of contacts 110a-e and contacts 210a-d can be reversed as well as intermixed. An electrochemical sensor 216 such as the carbon monoxide gas sensor part number 636240 available from Mine Safety Appliances Company of Pittsburgh, Pa. is preferably removably attached to the forward side of printed circuit board 214 via pronged contacts 218.

Printed circuit board 214 is preferably seated in a seating member 220 (for example, formed from an insulating polymeric material). Printed circuit board 214 can be properly aligned within seating member 220 via the cooperation of guides and notches (not shown) as described above. Preferably, a rearward facing surface of printed circuit board 214 abuts a flange or ledge 222 (see FIG. 5B) formed around the inner wall of seating member 220. A potting material as described above can also be used in connection with printed circuit board 214 and seating member 220.

Seating member 220 preferably includes radially outward extending tabs 224 that seat within a groove 230 (see FIG. 5B) formed in the interior wall of second housing section 200 so that seating member 220 is secured within second housing section 200 to prevent axial movement thereof relative to second housing section 200, but so that seating member 220 can rotate about axis A relative to second housing section 200. A wave spring 240 and a polymeric disk 242 preferably space sensor 216 away from gasket 250 until first housing section 100 and second housing section 200 are generally in full connection. In this manner, binding on gasket 250 can be prevented as housing section 200 rotates about axis A relative to seating member 200 during connection as described below.

Preferably, gas enters sensor assembly 10 through a flame arrestor such as metal frit 260 that is positioned on a forward end of second housing section 200. Gasket 250 creates a seal around sensor 216 and also assists in preventing potentially damaging gas(es) from the surrounding environment from coming into contact with the internal components of sensor assembly 10 other than sensor 216. Sensor assembly 10 can also include a sealing member such as O-ring 280 which seats in a channel of groove 270 formed in second housing section 200 to assist in forming an environmental seal.

During connection, housing section 200 is first generally aligned to be coaxial with housing section 100 and then brought into connection with housing section 100. Housing section 200 is then rotated about axis A relative to housing section 100 which can be fixed, for example, to wall 300. Seating member 220 rotates with housing section 200 until a radially inward extending abutment member 228 (see FIG. 4) comes into contact with a radially outward extending abutment member 132 (see FIG. 1) of seating member 120. Contact of abutment member 228 with abutment member 132 occurs when contacts 210a-d are in general alignment with contacts 110a-d. Alignment of contacts 210a-d with contacts 110a-d occurs as described above, regardless of the relative rotational alignment of housing sections 100 and 200 about axis A at the beginning of connection.

As second housing section 200 is further rotated relative to first housing section 100 to bring second housing section 200 into complete connection with first housing section 100. Contact of abutment member 228 with abutment member 132 maintains seating member 220 stationary relative to rotating housing section 200 and maintains contacts 210a-d in general alignment with contacts 110a-d. Additional assurance that electrical connection will be made only with proper alignment can be provided by polarizing one or more of corresponding contacts 110a-d and 210a-d by providing a unique orientation of one or more such contacts. In the embodiment of FIGS. 1 through 5B, for example, contacts 110a-c and contacts 210a-c are orientated to be tangential to a circle of a certain radius about axis A, while contact 110d and contact 210d are oriented to be in line with a radial line extending from axis A.

Further rotation of housing section 200 draws contacts 210a-d through slots 124a-d and into connection with contacts 110a-d. When contact between contacts 210a-d and contacts 110a-d is made, sufficient connection is made between second housing section 200 and first housing section 100 such that second housing section 200 and first housing section 100 form an explosion proof and/or flame proof enclosure therebetween. In that regard, an ignition source such as a spark that can occur when contacts 210a-d come into contact with contacts 110a-d under power is prevented from igniting gases in the surrounding environment. In general, it has been found that an explosion proof enclosure is formed between second housing section 200 and first housing section 100 when at least approximately six to eight threads or flights of threading of threaded section 208 are in contact with approximately six to eight flights of threading on section 108.

During disconnection, an explosion proof enclosure remains formed between second housing section 200 and first housing section 100 until contacts 210a-d are no longer in contact with contacts 110a-d. In that regard, to disconnect second housing section 200 from first housing section 100, second housing section 200 is rotated in a counter-clockwise direction relative to first housing section 100, thereby causing second housing section 200 to move axially forward relative to first housing section 100. After sufficient rotation of second housing section 200, contacts 210a-d will be drawn sufficiently forward to disconnect them from contacts 110a-d. At this point of disconnection, a sufficient number of flights of threads 208 of second housing section 200 are in connecting contact with threads 108 of first housing section 100 that first housing section 100 and second housing section 200 still form an explosion proof enclosure therebetween. Thus, any spark that might occur during disconnection is prevented from igniting any combustible gases in the surrounding environment.

Preferably, a protective covering is formed around each of contacts 110a-e, which still can be under power after disconnection from contacts 210a-d, to reduce the potential for sparking. In the embodiment of FIGS. 1 through 5B, forward, electrically insulating surface 125 of seating member 120 allows access to contacts 110a-e only through slots 124a-e thereof to reduce the risk of, for example, inadvertently contacting, damaging and/or short circuiting contacts 110a-e.

Threading connections afford one convenient manner of forming an explosion proof enclosure, but are not the only mode of forming an explosion proof enclosure. For example, FIGS. 6A through 7B illustrate a labyrinth type connection for a sensor assembly 400 including a first housing section 500 and a second housing section 600. Second housing section 600 includes a radially inward projecting key 610 that cooperates with a doglegged keyway 510 formed in the exterior wall of first housing section 500. In that regard, key 610 first travels axially in keyway 510 as second housing section 600 is moved axially toward first housing section 500. Second housing section 600 is then rotated in a clockwise direction about axis A' relative to first housing section 500 to seat key 610 within keyway 510 as illustrated in FIG. 6B.

First housing section 500 includes one or more spaced, generally cylindrical, axial projections 520a and 520b. Likewise, second housing section 600 includes one or more spaced, generally cylindrical, axial projections 620a and 620b. The outer wall of first housing section 500 and projections 520a and 520b cooperate with the outer wall of second housing section 600 and projections 620a and 620b to form a tortuous path or labyrinth through which an ignition source cannot escape to ignite any combustible gases in the surrounding environment.

As described above, each of first housing section 500 and second housing section 600 can be provided with electrical contacts that form a connection only when first housing section 500 and second housing section 600 form a sufficient connection to form an explosion proof connection therebetween. In that regard, the connection between first housing section 500 and second housing section 600 must be such that an ignition source (for example, an internal flame or an explosion resulting from a spark from connection between electrical contacts) cannot escape into the surrounding environment.

An explosion proof enclosure can also be formed between only the outer wall of, for example, first housing section 500 and the outer wall of second housing section 600 by having the inner diameter of the wall of second housing section 600 be only very slightly larger than the outer diameter of the wall of first housing section 500 such that an ignition source from within the enclosure is unable to ignite any combustible gases in the surrounding environment when a sufficient axial length of the wall of second housing section 600 encompasses the wall of first housing section 500. However, production of housing sections with such close or tight tolerances can be difficult and expensive.

Disconnection and/or connection between contact members of a first housing section and a second housing section of an instrument can be made by drawing the contacts together in an axial direction as described for contacts 110a-d and 210a-d. However, such mating contacts need not be brought into contact by axial motion. For example, as is clear to one skilled in the art, the contacts can be brought into connection by rotation of one set of contacts into connection with another set of contacts. As described above, cooperating associated with first housing section 500 and second housing section 600 are preferably automatically aligned with each other for connection during connection of first housing section 500 and second housing section 600.

While the present invention has been generally described in connection with instruments and instrument assemblies (for example, sensor assemblies), the present invention is also applicable in connecting and/or disconnecting any electrical connection (including, for example, wires or cables) under power.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A connector for use in an environment in which a combustible material may be present, comprising:
a first housing section including a plurality of electrically conductive contacts therein; and
a second housing section including a plurality of electrically conductive contacts that can form an electrical connection with the contacts of the first housing section, the first housing section and the second housing section being removably connectable, the first housing section and the second housing section being capable of forming an explosion proof housing when connected, the second housing section comprising a seating member to which the contacts of the second housing section are attached, the seating member being movably attached to the second housing member such that the contacts of the second housing section move after contact of the second housing section with the first housing section relative to the contacts of the first housing section to automatically align the contacts of the second housing and the contacts of the first housing section during connection of the second housing section to the first housing section regardless of the rotational orientation of the contacts of the first housing section about the axis of the connector relative to the contacts of the second housing section upon contact of the second housing section with the first housing section, electrically conductive connection between the contacts of the first housing section and the contacts of the second housing section occurring during connection of the second housing section to the first housing section in a manner such that when connection between the contacts of the first housing section and the contacts of the second housing section occurs, the first housing section and the second housing section are in sufficient connection to form an explosion proof housing.

2. The connector of claim 1 wherein the contacts of the first housing section are in electrical connection with a first cable and the contacts of the second housing section are in electrical connection with a second cable.

3. The connector of claim 1 wherein one of the first housing section and the second housing section includes at least one instrument component in electrical connection with the contacts of that housing and at least one of the contacts of the other of the first housing section and the second housing section is adapted to transmit electrical power to the instrument component when the first housing section and the second housing section are connected.

4. The connector of claim 1 wherein the contacts of the first housing section are recessed in a nonconductive cover.

5. The connector of claim 1 wherein the plurality of electrically-conductive contacts comprises a power connection, a ground connection and a data connection.

6. The connector of claim 1 wherein the electrically-conductive contacts of the first housing are receptacles and the electrically-conductive contacts of the second housing are pins.

7. The connector of claim 1 wherein electrical connection between the contacts of the first housing section and the second housing section is broken during disconnection of the second housing section from the first housing section in a manner such that when disconnection between the contacts of the first housing section and the contacts of second housing section occurs, the first housing section and the second housing section remain in sufficient connection to form an explosion-proof housing.

8. The connector of claim 7 wherein the second housing section is moved axially away from the first housing section during disconnection and the second housing section is moved axially toward the first housing section during connection.

9. The connector of claim 8 wherein the second housing section includes threading that cooperates with threading on the first housing section so that rotating the second housing section relative to the first housing section causes relative axial movement between the second housing section and the first housing section.

10. The connector of claim 9 wherein the contacts of the first housing section are recessed in a nonconductive cover.

11. A method of forming a connection between electrically conductive contacts in an environment in which a combustible gas may be present, comprising:
    connecting a second housing section, including a plurality of electrically conductive contacts that can form an electrical connection with a plurality of electrically conductive contacts of a first housing section, to the first housing section;
    permitting at least one of the plurality of contacts of the second housing section and the plurality of contacts of the first housing section to move relative to the contacts of the other of the second housing section and the contacts of the first housing section to automatically align the contacts of the second housing section and the contacts of the first housing section after contact of the second housing section and the first housing section and during connection of the second housing section to the first housing section regardless of the rotational orientation of the contacts of the first housing section about an axis relative to the contacts of the second housing section prior to contact of the second housing section with the first housing section, and
    making electrically conductive connection between the contacts of the second housing section and the contacts of the first housing section during connection of the second housing section to the first housing section in a manner such that when connection between the contacts of the first housing section and the contacts of second housing section occurs, the first housing section and the second housing section are in sufficient connection to form an explosion proof housing further comprising breaking the electrical connection between the contacts of the first housing section and the contacts of the second housing section such that when disconnection between the contacts occurs, the first housing section and the second housing section remain in sufficient connection to form an explosion-proof housing.

12. A gas sensor assembly for use in an environment in which a combustible gas may be present, comprising:
    a first housing section including a plurality of electrically conductive contacts therein; at least one of the contacts of the first housing section being electrical connectible to a power source; and
    a second housing section including a plurality of electrically conductive contacts that can form an electrical connection with the contacts of the first housing section, at least one of the contacts of the second housing section being in electrical contact with a gas sensor, the first housing section and the second housing section being removably connectable, the first housing section and the second housing section being capable of forming an explosion proof housing when connected, the second housing section comprising a seating member to which the contacts of the second housing section are attached, the seating member being movably attached to the second housing member such that the contacts of the second housing move relative to the contacts of the other of the second housing section and the first housing section to automatically align the contacts of the second housing and the contacts of the first housing section after contact of the second housing section with the first housing section and during connection of the second housing section to the first housing section regardless of the rotational orientation of the contacts of the first housing section about an axis relative to the contacts of the second housing section prior to connection of the second housing section to the first housing section, electrically conductive connection between the contacts of the first housing section and the contacts of the second housing section occurring during connection of the second housing section to the first housing section in a manner such that when connection between the contacts of the first housing section and the contacts of second housing section occurs, the first housing section and the second housing section are in sufficient connection to form an explosion proof housing.

13. The gas sensor assembly of claim 12 wherein the plurality of electrically-conductive contacts comprises a power connection, a ground connection and a data connection.

14. The gas sensor assembly of claim 12 wherein the electrically-conductive contacts of the first housing are receptacles and the electrically-conductive contacts of the second housing are pins.

15. The gas sensor assembly of claim 12 wherein electrical connection between the contacts of the first housing section and the second housing section is broken during disconnection of the second housing section from the first housing section in a manner such that when disconnection between the contacts of the first housing section and the contacts of second housing section occurs, the first housing section and the second housing section remain in sufficient connection to form an explosion proof housing.

16. The gas sensor assembly of claim 15 wherein the second housing section is moved axially away from the first housing section during disconnection and the second housing section is moved axially toward the first housing section during connection.

17. The gas sensor assembly of claim 16 wherein the second housing section includes threading that cooperates with threading on the first housing section so that rotating the second housing section relative to the first housing section causes relative axial movement between the second housing section and the first housing section.

18. The gas sensor of claim 17 wherein the contacts of the second housing section rotate relative to the contacts of the first housing section to align with the contacts of the first housing section during connection of the second housing section to the first housing section.

19. The gas sensor of claim 18 wherein the contacts of the first housing section are seated in a slotted, protective cover.

* * * * *